United States Patent
Karol et al.

(10) Patent No.: US 6,635,696 B1
(45) Date of Patent: Oct. 21, 2003

(54) CURING COMPOUND AND METHOD OF CURING HALOGENATED POLYMERS

(75) Inventors: Thomas J. Karol, Norwalk, CT (US); Francis S. Cheng, West Hartford, CT (US)

(73) Assignee: R.T. Vanderbilt Company, Inc., Norwalk, CT (US)

( * ) Notice: Subject to any disclaimer, the term of this patent is extended or adjusted under 35 U.S.C. 154(b) by 287 days.

(21) Appl. No.: 09/726,344

(22) Filed: Dec. 1, 2000

(51) Int. Cl.[7] .................................................. C08K 5/45
(52) U.S. Cl. ........................ 524/84; 525/373; 544/359; 548/148; 508/274
(58) Field of Search ........................ 548/142; 508/274; 524/84; 525/373; 544/359

(56) References Cited

U.S. PATENT DOCUMENTS 6,255,259 B1    7/2001   Camenzind ................. 508/271

*Primary Examiner*—Peter D. Mulcahy
(74) *Attorney, Agent, or Firm*—Norris McLaughlin & Marcus

(57) ABSTRACT

Additives including dithiocarbamyl derivatives of 2,5-dimercapto-1,3,4-thiadiazole (DMTD) useful as curing agents and accelerators. Curable polymer compositions including at least one halogenated polymer and at least one additive including the dithiocarbamyl DMTD derivatives. A method is also disclosed for preparing a cured polymer by admixing at least one halogenated polymer with at least one additive including the dithiocarbamyl DMTD derivatives and subsequently curing the composition.

31 Claims, No Drawings

CURING COMPOUND AND METHOD OF CURING HALOGENATED POLYMERS

BACKGROUND OF INVENTION

The present invention relates to thiadiazole derivatives useful as accelerators and/or curing agents for halogenated polymers in rubber vulcanization processes, and to halogenated polymer compositions containing the thiadiazole derivatives, as well as a method of preparing the same.

Vulcanizable rubber compositions present certain inherent problems in terms of handling and storage. For example, prior to the curing, the uncured rubber may often degrade during storage due to hydrolytic instability of the additives contained therein. As a result the cure reproducibility from batch to batch in the vulcanization process can often vary. However, batch-to-batch cure reproducibility is an important parameter of quality control.

It is known that halogen-containing polymers may be compounded with curing agents, accelerators and other compounds in order to prepare vulcanizable rubber compositions which are useful in a variety of applications. A description of curing agents and accelerators, as well as other components of natural and synthetic rubbers can be found in Kirk-Othmer's Encyclopedia of Chemical Technology, John Wiley & Sons, 4th Edition, at pages 460–481.

Despite the availability of curing agents and/or accelerators for halogenated polymers, there is a continuing need for curing agents and/or accelerators that allow for good bin storage characteristics and improved batch-to-batch cure reproducibility.

Accordingly, it is an object of the present invention to compounds useful as curing agents and/or accelerators for rubber vulcanization processes which provide good bin storage properties for uncured rubber and improved consistency in cure reproducibility.

It is yet another object of the present invention to provide curable rubber compositions which exhibit good bin storage properties and improved consistency in cure reproducibility and methods of preparing the cured rubber compositions.

SUMMARY OF THE INVENTION

In accordance with the present invention, an additive is provided including a dithiocarbamyl-1,3,4,-thiadiazole derivative having formula (I), or an isomer thereof:

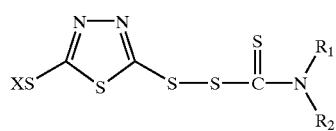
(I)

where $R_1$ and $R_2$ are independently a radical being either an alkyl, a cycloalkyl, an alkenyl, an aryl, an arylalkyl, or an alkylaryl, or $R_1$ and $R_2$ together form a 3- to 7-membered cyclic ring structure; and X is (i) hydrogen, (ii) a dithiocarbamyl radical having formula (II):

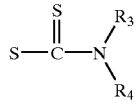
(II)

where $R_3$ and $R_4$ are independently a radical being either an alkyl, a cycloalkyl, an alkenyl, an aryl, an arylalkyl, or an alkylaryl, or $R_3$ and $R_4$ together form 3- to 7-membered cyclic ring structure, or (iii) a mixture thereof. In a preferred embodiment, X is hydrogen, and $R_1$ and $R_2$ are independently a radical being either an ethyl, an isopropyl, a butyl, or an isobutyl, or $R_1$ and $R_2$ together form a 6-membered cyclic ring structure, with a piperidyl radical being preferred.

In another embodiment the present invention provides an additive including a dithiocarbamyl-bis-1,3,4,-thiadiazole derivative having formula (III), or an isomer thereof:

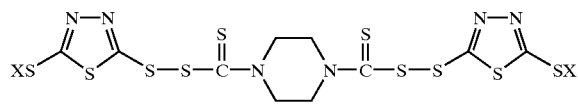
(III)

where X is hydrogen or a dithiocarbamyl radical having formula (II)

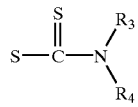
(II)

where $R_3$ and $R_4$ are independently a radical being either an alkyl, a cycloalkyl, an alkenyl, an aryl, an arylalkyl, or an alkylaryl, or $R_3$ and $R_4$ together form 3- to 7-membered cyclic ring structure. In a preferred embodiment, X is hydrogen.

The present invention also provides a curable polymer composition including at least one halogenated polymer and at least one of the above-described additives of the present invention. A method is also provided for preparing a cured polymer composition including at least one halogenated polymer and at least one of the additives of the invention.

The additives of the present invention are particularly useful as curing agents and/or accelerators for halogen-containing polymer compositions, and provide good bin storage characteristics for the uncured polymer composition and improved cure reproducibility. These and other advantages of the present invention will be more readily apparent from the detailed description set forth below.

DETAILED DESCRIPTION OF THE INVENTION

It has now been discovered that certain hydrocarbyl dithiocarbamyl-1,3,4-thiadiazole derivatives having a disulfide linkage are useful as curing agents and accelerators in halogen-containing polymer compositions. The thiadiazole derivatives of the present invention have been found to provide good bin storage characteristics and improved cure reproducibility when used as additives in halogen-containing polymer compositions.

In one embodiment an additive is provided that includes a dithiocarbamyl-1,3,4,-thiadiazole derivative having formula (I):

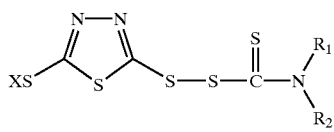
(I)

where $R_1$ and $R_2$ are independently a radical being either an alkyl, a cycloalkyl, an alkenyl, an aryl, an arylalkyl, or an alkylaryl, or $R_1$ and $R_2$ together form a 3- to 7-membered cyclic ring structure; and X is (i) hydrogen, (ii) a dithiocarbamyl (i.e., DTC) radical having formula (II):

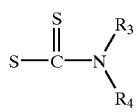
(II)

where $R_3$ and $R_4$ are independently a radical being either an alkyl, a cycloalkyl, an alkenyl, an aryl, an arylalkyl, or an alkylaryl, or $R_3$ and $R_4$ together form substituted or unsubstituted 3- to 7-membered cyclic ring structure, or (iii) a mixture thereof. Preferably, X is hydrogen while $R_1$ and $R_2$ are independently a $C_1$ to $C_5$ alkyl radical such as an ethyl, an isopropyl, a butyl, or an isobutyl, or $R_1$ and $R_2$ together form a substituted or unsubstituted 6-membered cyclic ring structure (e.g., a piperidyl radical).

In another embodiment the present invention provides an additive that includes a dithiocarbamyl-bis-1,3,4,-thiadiazole derivative having formula (III):

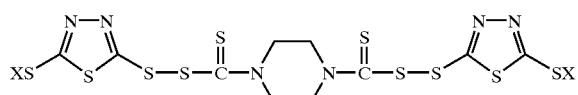
(III)

where X is (i) hydrogen, (ii) a dithiocarbamyl radical having formula (II):

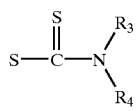
(II)

where $R_3$ and $R_4$ are independently a radical being either an alkyl, a cycloalkyl, an alkenyl, an aryl, an arylalkyl, or an alkylaryl, or $R_3$ and $R_4$ together form 3- to 7-membered cyclic ring structure, or (iii) a mixture thereof. In a preferred embodiment, X is hydrogen.

The derivatives of formulas (I) and (III) are synthesized following techniques known in the art. For example, compounds having formula (I) can be synthesized by reacting 2,5-dimercapto-1,3,4,-thiadiazole (i.e., DMTD) with a dithiocarbamic acid in which the amine moiety is a tertiary amine having substituents $R_1$ and $R_2$, or $R_3$ and $R_4$. The reaction is carried out in the presence of an oxidizing agent (e.g., hydrogen peroxide). As known in the art, dithiocarbamic acid is not readily isolatable and thus needs to be formed in situ to provide the starting material. The dithiocarbamic acid intermediate is synthesized in situ by reacting carbon disulfide with the appropriate secondary amine (e.g., dibutyl amine to form dibutyl dithiocarbamic acid). Likewise, compounds of formula (III) where X is hydrogen can be synthesized by first forming in situ bis-(1,4-piperazine dithiocarbamic acid) from homopiperazine and carbon disulfide. The dithiocarbamic acid intermediate is then reacted with 2,5-dimercapto-1,3,4-thiadiazole in the presence of an oxidizing agent. The reaction conditions (e.g., temperature and time) are variable and can be easily modified by one of ordinary skill in the art following the teachings set forth herein.

While not wishing to be limited by theory, those skilled in the art will recognize that the additives of the invention may additionally contain positional isomers of the derivatives having formulas (I) and (III) due to tautomerization or other similar rearrangement of the substituents on the DMTD moiety. In accordance with the invention, reference to "an isomer thereof" means positional isomers. Positional isomers of formulas (I) and (III) are also useful as curing agents and accelerators. Positional isomers of formula (I) would have the following structures:

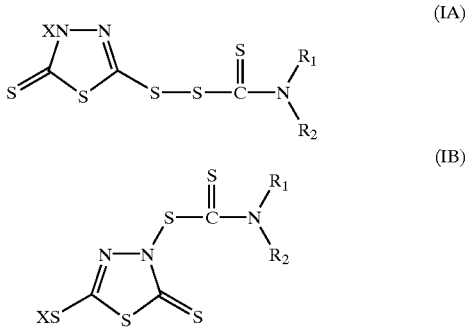

Likewise, similar rearrangements for compounds having formula (III) are also expected.

The above-described additives of the invention, alone or in combination, are admixed with a major amount of at least one halogenated polymer to provide a curable (i.e., vulcanizable) polymer composition. The polymer composition is then cured following conventional techniques known in the art to produce a cured (i.e., vulcanized) polymer composition.

In accordance with the present invention, any saturated or unsaturated halogen-containing (i.e., halogenated) polymer may be used. Preferably, the polymer contains at least one percent by weight halogen with about five percent being more preferred. The halogen content in the polymer may range up to 40 percent based on the weight of the polymer. Preferably, the halogen-containing polymers is an elastomer. In another preferred embodiment, the halogen-containing polymer is a chlorine-containing (i.e., chlorinated) polymer. Representative examples of chlorine-containing polymers to be used in accordance with the present invention include, but are not limited to, homopolymers of epichlorohydrin, copolymers of epichlorohydrin and ethylene oxide or propylene oxide, polychloroprene, chlorinated polyolefins, chlorosulfonated polyolefin, polychloroalkylacrylates and chlorobutyl rubber. These polymers are well known in the art and are available commercially from variety of sources.

One particularly preferred chlorinated polymer is chlorinated polyethylene "CPE" which is commercially available from DuPont Dow under the tradename Tyrin®.

The halogen-containing polymers may be blended with non-halogen containing polymers as along as a sufficient halogen content is provided in the polymer composition to effect crosslinking. The blends can include, but are not limited to, natural ruber, polybutadiene, polyolefins, copolymers of butadiene with styrene (SBR) or acrylonitrile (NBR), copolymers of ethylene-propylene-diene (EPDM), butyl rubber and the like. Such blends may contain from about 10 to about 90% by weight of each type of polymer. In a more preferred embodiment, the blends contain the halogenated polymer at levels from about 25 to 75% by weight with respect to the total weight of the polymer blend.

The additives of the invention may be incorporated into the polymer composition in their pure form or they may be mixed with one or more liquid diluents. They also may be adsorbed onto the surface of a finely divided, inert carrier to provide a powdered product. When the additives of the invention are mixed with a liquid diluent or finely divided carrier, the additive may range from 15 to 85 percent by weight of the composition with the remainder being the diluent, carrier or a combination thereof. Preferably, the additives of the invention are mixed in a ratio ranging from 30 to 70 percent by weight.

The suitable diluents, among others, include aromatic, naphthenic and paraffinic hydrocarbon oil, polyglycols and glycols, alkyl esters of dibasic acids, e.g., dioctyl phthalate, dioctyl sebacate, dioctyl adipate, diisodecyl glutarate, dioctyl azolate, alkyl sulfides, fatty acid esters, e.g., butyl oleate, butyl stearate, octyl epoxy tallate, trioctyl trimellitate, polyester plasticizers, e.g., polymeric di(butoxy-ethoxy-ethyl)adipate, polymers of bis (ethyleneoxy)methane with disulfide linkages; petroleum sulfonates, alkyl trimellitates; and polymeric esters.

The suitable finely divided carrier materials include carbon black, metal oxides, such as aluminum oxide, alumina, silica, mineral fillers, such as clay, talc and betonite, aluminosilicate, zeolites, calcium silicate and similar carriers. Preferred carriers have a surface area of from about 75 to about 300 m²/gm. A particularly preferred carrier is amorphous silica available from Pittsburgh Plate Glass Company under the tradename HISIL®233 and HISIL® ABS.

The amount of the additive effective to cure the chlorinated polymer will vary as a function of the halogen content in the halogenated polymer. Generally, the additives are employed in the range from about 0.1 to about 10.0 parts by weight per 100 parts by weight of halogenated polymer present in the curable composition. More preferably, the additives of the present invention are present in the amount from about 0.5 to about 5.0 parts by weight per 100 parts by weight of the halogenated polymer. If a diluent or a carrier material is added to the curable polymer composition, higher levels of the additive may be required.

Additional accelerators of the aliphatic or aromatic amine type can also be used if the halogenated polymer employed for production of vulcanized rubber is relatively unreactive. The suitable accelerators, among others, include the reaction product of butyraldehyde and aniline (available commercially under the tradename VANAX® RTM 808 from R. T. Vanderbilt Company, Inc.), fatty amines, sulfonamides such as N-cyclohexyl-2-benzothiazolesulfenamide (available commercially under the tradename DURAX® from R. T. Vanderbilt Company, Inc.) and quaternary ammonium salts, such as tetrabutylammonium bromide and tetraethylammonium chloride. A listing of additional accelerators to be utilized in accordance with the present invention is set forth in "Rubber Chemicals," J. Van Alphen, pages 1–46 (1973), which is incorporated herein by reference.

For curing blends of halogenated and non-halogenated polymers, sulfur or other well known sulfur-containing curatives for unsaturated elastomers may be included in the composition. Examples of such compounds include, but are not limited to, sulfur, benzothiazyl disulfide, N-oxydiethylene benzothiazole-2-sulfonamide, 2-mercaptobenzo-thiazole, alkyl phenol disulfides, tetraalkylthiuram disulfide and monosulfide having normal or branched chain alkyl groups, m-phenylene-bismaleimide and N,N'-diarylguanidines.

Other additives, which may be desirable to effect crosslinking along with the derivatives of the present invention, include basic metal oxides, metal hydroxides and metal salts of carboxylic acids. The typical additives include zinc oxide, magnesium oxide, zinc stearate and sodium acetate. The magnesium oxide may be synthetic or a natural magnesite mineral. The magnesite may be calcined or treated by other similar processes to yield a predominantly magnesium oxide product.

In addition to the curatives, the polymer compositions of the invention may also include antioxidants, for example, octylated diphenylamine, diphenyl-p-phenylenediamine and styrenated phenol type antioxidants. Likewise, the polymer compositions of the invention may include antidegradants, antiozonants, antiflexcracking agents, heat stabilizers and metal poison-inhibitors, which are well known in the art.

The curable compositions may be prepared and blended using any suitable mixing device such as a two-roll mill, an internal mixer (Brabender Plasticorder), a Banbury Mixer, a kneader or a similar mixing device. The processing and vulcanization techniques are well known in the art.

The following non-limiting examples are given to further illustrate the additives of the invention and their use in curable polymer compositions. All percentages and parts are based on weight unless otherwise indicated.

EXAMPLE 1

Diisopropyl DTC DMTD

5'-(Diisopropyldithiocarbamyl)-2,5-dimercapto-1,3,4-thiadiazole (i.e., formula (I) where X is hydrogen and $R_1$ and $R_2$ are isopropyl radicals) was prepared in the following manner. In 100 grams of isopropyl alcohol 20.5 grams of diisopropylamine was combined with 16 grams of carbon disulfide ($CS_2$) and held at a temperature of about 27° C. for about 1 hour to yield a diisopropyl dithiocarbamic acid intermediate. Subsequently, 30 g of a 2,5-dimercapto-1,3,4-thiadiazole was added to the mixture along of 20 g of 35 wt. % hydrogen peroxide. The mixture was reacted for about 1 hour at a temperature of about 28° C. to yield the solid end product 5'-(diisopropyldithiocarbamyl)-2,5-dimercapto-1,3, 4-thiadiazole. The isopropyl alcohol was filtered off and saved for recovery.

EXAMPLE 2

Di-n-butyl DTC DMTD

5'-(Dibutyldithiocarbamyl)-2,5-dimercapto-1,3,4-thiadiazole (i.e., formula (I) where X is hydrogen and $R_1$ and $R_2$ are n-butyl radicals) was prepared in the following manner. In 100 grams of isopropyl alcohol 26 grams of dibutyl amine was combined with 16 grams of $CS_2$ and held at a temperature of about 40° C. for about 1 hour to yield a dibutyl dithiocarbamic acid intermediate. Subsequently, 30 grams of 2,5-dimercapto-1,3,4-thiadiazole was added to the mixture along with 20 grams of 35 wt. % hydrogen peroxide. The mixture was reacted for about 1 hour at a temperature of about 28° C. to yield the liquid end product 5'-(dibutyldithiocarbamyl)-2,5-dimercapto-1,3,4-thiadiazole.

EXAMPLE 3

Piperidyl DTC DMTD

5'-(Piperidyldithiocarbamyl)-2,5-dimercapto-1,3,4-thiadiazole (i.e., formula (I) where X is hydrogen and $R_1$ and $R_2$ form a six-membered ring) was prepared in the following manner. In 100 grams of isopropyl alcohol 17 grams of piperidine was combined with 16 grams of $CS_2$ and held at a temperature of about 35° C. for about 1 hour to yield a piperidyl dithiocarbamic acid intermediate. Subsequently, 30 grams of 2,5-dimercapto-1,3,4-thiadiazole was added to the mixture along with 20 grams of 35 wt. % hydrogen peroxide. The mixture was reacted for about 1 hour at a temperature of about 35° C. to yield the solid end product 5'-(piperidyldithiocarbamyl)-2,5-dimercapto-1,3,4-thiadiazole. The isopropyl alcohol was filtered off and saved for recovery.

EXAMPLE 4

Diethyl DTC DMTD

5'-(Diethyldithiocarbamyl)-2,5-dimercapto-1,3,4-thiadiazole (i.e., formula (1) where X is hydrogen and $R_1$ and $R_2$ are ethyl radicals) was prepared in the following manner. In 100 grams of isopropyl alcohol 20.5 grams of diethylamine was combined with 16 grams of carbon disulfide ($CS_2$) and held at a temperature of about 27° C. for about 1 hour to yield a diethyl dithiocarbamic acid intermediate. Subsequently, 30 g of a 2,5-dimercapto-1,3,4-thiadiazole was added to the mixture along of 20 g of 35 wt. % hydrogen peroxide. The mixture was reacted for about 1 hour at a temperature of about 28° C. to yield the solid end product 5'-(diethyldithiocarbamyl)-2,5-dimercapto-1,3,4-thiadiazole. The isopropyl alcohol was filtered off and saved for recovery.

EXAMPLE 5

Vulcanizates incorporating the derivatives of Example 1–4 were prepared and evaluated. Samples were prepared by compounding chloropolyethylene polymer with the derivatives of Example 1–4 (neat) and various other additives as listed in Table 1 below.

TABLE 1

| Sample | 1 | 2 | 3 | 4 | 5 | 6 | 7 |
|---|---|---|---|---|---|---|---|
| Components (parts by weight) | | | | | | | |
| Chloropolyethylene[(1)] | 100 | 100 | 100 | 100 | 100 | 100 | 100 |
| Carbon Black[(2)] | 50 | 50 | 50 | 50 | 50 | 50 | 50 |
| Magnesium Oxide[(3)] | 5 | 5 | 5 | 5 | 5 | 5 | 5 |
| Process oil[(4)] | 30 | 30 | 30 | 30 | 30 | 30 | 30 |
| Amine Activator[(5)] | 0.8 | 0.8 | 0.8 | 0.8 | 0.8 | — | — |
| Retarding Agent[(6)] | | | | | 0.5 | | |
| Inventive Curative | | | | | | | |
| Diisopropyl DTC DMTD | 2.5 | | | | 2.5 | | |

TABLE 1-continued

| Sample | 1 | 2 | 3 | 4 | 5 | 6 | 7 |
|---|---|---|---|---|---|---|---|
| Di-n-butyl DTC DMTD | | 2.5 | | | | 2.5 | |
| Piperidyl DTC DMTD | | | 2.5 | | | | |
| Diethyl DTC DMTD | | | | 2.5 | | | 2.5 |
| Total Parts: | 188.3 | 188.3 | 188.3 | 188.3 | 188.8 | 187.8 | 187.8 |

[(1)]Commercially available from DuPont Dow Elastomer as Tyrin ® CM0136.
[(2)]Commercially available from Degussa Chemical as N774.
[(3)]Commercially available from Marine Magnesium Company as Maglite ® D.
[(4)]Commercially available from Sun Oil and Refining Company as Sundex ® 790
[(5)]Commercially available from R.T. Vanderbilt Company, Inc., as Vanax ® 882B.
[(6)]N-(cyclohexylthio)phthalimide - commercially available from R.T. Vanderbilt Company, Inc., as Vantard ® PVI.

The compositions were pressed cured at 171° C. for 30 minutes. The samples were evaluated for Torque and Scorch time by ASTM D2084. The Torque and Scorch results for the samples are listed in Table 2 below.

TABLE 2

| Sample | 1 | 2 | 3 | 4 | 5 | 6 | 7 |
|---|---|---|---|---|---|---|---|
| Oscillating Disk Rheometer - 60 minutes @ 171° C. | | | | | | | |
| Minimum Torque (ML) (inch-pounds) | 2.6 | 2.9 | 2.0 | 0.6 | 2.9 | 3.2 | 3.5 |
| Maximum Torque (MH) (inch-pounds) | 46.4 | 49.2 | 43.9 | 53.9 | 45.6 | 44.3 | 49.4 |
| Scorch time, (ts2) (minutes) | 1.0 | 1.4 | 2.9 | 1.7 | 1.6 | 1.2 | 1.3 |
| Cure time, (tc90) (minutes) | 15.5 | 11.5 | 27.5 | 22.5 | 10.5 | 19.0 | 24.0 |

EXAMPLE 6

A comparative study was conducted to evaluate bin-storage stability of vulcanizable composition compounded with di-n-butyl DTC DMTD produced in accordance with Example 2 and the curative "Echo A" which is commercially available from Hercules, Inc. Echo A, CAS. No. 51988-14-8, is known in the art as 2,5-dimercapto-1,3,4-thiadiazole monobenzoate ester which corresponds to the structure:

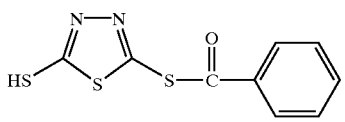

Samples were prepared by compounding the components listed in Table 3. Differing amounts of Echo A and di-n-butyl DTC DMTD were utilized to provide an equimolar ratio of thiadiazole moiety due to differing molecular weights of the curatives. Likewise, differing amounts of the accelerators Vanax® 808 Liquid and Durax® were also utilized provide an equimolar ratio of accelerator.

TABLE 3

| Components (parts by weight) | Samples | | | | |
|---|---|---|---|---|---|
| | 8 | 9 | 10 | 11 | 12 |
| Tyrin ® CPEO136 | 100 | 100 | 100 | 100 | 100 |
| N650[(1)] | 40 | 40 | 40 | 40 | 40 |
| Atomite ® Whiting[(2)] | 75 | 75 | 75 | 75 | 75 |
| Dioctyl phthalate (DOP) | 15 | 15 | 15 | 15 | 15 |
| Sundex ® 790 | 20 | 20 | 20 | 20 | 20 |
| Elastomag ® 170[(3)] | 7.5 | 10 | 5 | 5 | 10 |
| Carbowax ® 3350[(4)] | 1 | 1 | 1 | 1 | 1 |
| PE617A[(5)] | 2 | 2 | 2 | 2 | 2 |
| Di-n-butyl DTC DMTD | — | 5.02 | 5.02 | 5.02 | 5.02 |
| Echo A | 2.5 | — | — | — | — |
| Vanax ® 808 Liquid[(6)] | 0.8 | — | — | — | — |
| Durax 200[(7)] | — | 1.5 | 1.5 | 0.5 | 0.5 |
| Total Parts: | 263.8 | 269.5 | 264.5 | 263.5 | 268.5 |

[(1)]Carbon Black commercially available from Degussa Chemical.
[(2)]Calcium carbonate commercially available from Thompson & Weinman.
[(3)]Magnesium oxide commercially available from Elastochem.
[(4)]Polyethylene glycol commercially available from Union Carbide.
[(5)]Low molecular weight polyethylene commercially available from Allied Signal, Inc.
[(6)]Accclerator (butrylaldehyde-amine condensation adduct) commercially available from R. T. Vanderbilt Company, Inc.
[(7)]Accclerator (N-cyclohexyl-2-benzothiazolesulfenamide) commercially available from R. T. Vanderbilt Company. Inc.

Samples were evaluated for Mooney Parameters using a small rotor (MS), Torque and Scorch times, and Physical properties, with the results being listed Table 4.

TABLE 4

| | Sample | | | | |
|---|---|---|---|---|---|
| | 8 | 9 | 10 | 11 | 12 |
| Mooney Scorch, MS@121° C. | | | | | |
| Initial Viscosity (MU) | 42.34 | 41.97 | 42.13 | 42.94 | 43.37 |
| Minimum Viscosity (MU) | 29.8 | 29.12 | 28.93 | 31.15 | 31.25 |
| Final Viscosity (MU) | 44.82 | 44.15 | 43.94 | 46.17 | 46.27 |
| Mooney Scorch, MS@121° C. Aged 14 days at 40° C./95% relative humidity | | | | | |
| Initial Viscosity (MU) | 145.32 | 69.45 | 79.18 | 89.42 | 76.9 |
| Minimum Viscosity (MU) | 70.78 | 38.35 | 43.99 | 54.65 | 46.84 |
| Final Viscosity (MU) | 86.07 | 48.24 | 56.69 | 62.91 | 52.8 |
| Change Initial Viscosity (MU) | 102.98 | 27.48 | 37.05 | 46.48 | 33.53 |
| Change Minimum Viscosity (MU) | 40.98 | 9.23 | 15.06 | 23.5 | 15.59 |
| Oscillating Disk Rheometer - 60 minutes @ 160° C. | | | | | |
| Minimum Torque (ML) (dNm) | 2.02 | 1.98 | 2.14 | 1.98 | 2.06 |
| Maximum Torque (MH) (dNm) | 20.28 | 19.13 | 22.79 | 19.43 | 17.49 |
| Scorch time (ts2) (minutes) | 1.82 | 1.85 | 1.45 | 1.27 | 1.64 |
| Cure time (tc90) (minutes) | 6.6 | 27.96 | 27.42 | 24.08 | 25.84 |
| Physical Properties @ RT - Cure t95 + 5.0 Minutes - 160° C. | | | | | |
| Hardness - Shore A | 76 | 72 | 73 | 72 | 74 |
| Tensile Break (MPa) | 11.25 | 12.15 | 12.52 | 12.87 | 11.52 |
| Elongation Break (%) | 341.9 | 407.8 | 405.4 | 418.8 | 435.9 |
| 200% Modulus (MPa) | 7.4 | 7.03 | 6.93 | 6.77 | 6.47 |

Apparent from Table 4, samples incorporating the derivatives of the invention as a curative exhibited significantly improved stability over the sample containing Echo A, which is considered the standard curative for halogenated polymers. For example, the comparative sample containing Echo A (sample 8) exhibited an increase in initial viscosity of 102.98 Mooney units (MU) after being stored for 14 days. To the contrary, the inventive samples (samples 9–12) exhibited increases in initial viscosity of only 27.48, 37.05, 46.48 and 33.53, respectively. Similar improvements in the change of minimum viscosity were also exhibited.

EXAMPLE 7

S,S'-DMTD-bis(Piperazinyl DTC Disulfide

S,S'-(2-thio-5-mercapto-1,3,4-thiadiazole)-bis(1,4-piperazine-dithiocarbamate disulfide) (i.e., formula (III) where X is hydrogen) was prepared in the following manner. 17.2 grams of piperazine was combined with 30.4 grams of $CS_2$ in a solvent mixture of 70 grams water and 150 grams of isopropyl alcohol. The mixture was held for about 1 hour at 30° C. to yield a bis(1,4-piperazinedithiocarbamic acid) intermediate. Subsequently, 60 grams of 2,5-dimercapto-1,3,4-thiadiazole was added to the mixture along with 38.9 grams of 35 wt. % hydrogen peroxide. The mixture was reacted for about 3 hours at 42° C. to yield the solid end product S,S '-(2-thio-5-mercapto-1,3,4-thiadiazole)-bis(1,4-piperazine-dithiocarbamate disulfide).

EXAMPLE 8

A study was conducted to evaluate S,S'-DMTD-bis (Piperazinyl DTC Disulfide) prepared in accordance with Example 7 with the di-n-butyl DTC DMTD prepared in accordance with Example 2. The samples were prepared by compounding the components listed in Table 5.

TABLE 5

| | Sample | |
|---|---|---|
| Components (parts by weight) | 13 | 14 |
| Tyrin ® CMO136 | 100 | 100 |
| N774 | 50 | 50 |
| Maglite ® D | 5 | 5 |
| Sundex ® 790 | 30 | 30 |
| Durax ® | 1 | 1 |
| S,S'-DMTD-bis(Piperazinyl DTC Disulfide) | 2.5 | |
| Di-n-butyl DTC DMTD | | 5.0* |

*To provide an equivalent ratio of thiadiazole moiety.

The compositions were pressed cured at 171° C. for 30 minutes. The samples were evaluated for Torque and scorch time by ASTM D2084 and Mooney parameters by ASTM D1646 using a small rotor (MS). The results are listed in Table 6 below.

TABLE 6

| Sample | 13 | 14 |
|---|---|---|
| Mooney Scorch, MS @ 121° C. | | |
| Minimum Viscosity, t5 (minutes) | 39.9 | 40.6 |
| Scorch, t5 (minutes) | 28.0 | 8.0 |
| Oscillating Disk Rheometer @ 171° C. | | |
| Minimum Torque (inch-pounds) | 0.7 | 0.7 |
| Maximum Torque (inch-pounds) | 10.7 | 10.5 |
| Scorch time (ts2) | 8.7 | 1.6 |
| Cure time (tc90) (minutes) | 41.6 | 26.3 |

EXAMPLE 9

The combined effectiveness of S,S'-DMTD-bis (Piperazinyl DTC Disulfide) prepared in accordance with Example 7 with the di-n-butyl DTC DMTD prepared in accordance with Example 2 was evaluated. The sample was prepared by compounding the components listed in Table 7.

TABLE 7

| Components (parts by weight) | Sample 15 |
|---|---|
| Tyrin ® CMO136 | 100 |
| N774 | 50 |
| Maglite ® D | 5 |
| Sundex ® 790 | 30 |
| Durax ® | 1 |
| S,S'-DMTD-bis(Piperazinyl DTC Disulfide) | 2.5 |
| Di-n-butyl DTC DMTD | 1.25 |

A portion of the unaged sample was vulcanized, while another portion was aged for 7 days at 37.8° C. at 100% relative humidity(RH). The vulcanizates were formed by press curing for 30 minutes at 171° C. Mooney parameters, Scorch time and Torque were evaluated as in Example 8. The results are listed in Table 8.

TABLE 8

| Sample | 15-Unaged | 15-Aged |
|---|---|---|
| Mooney Scorch, MS @ 121° C. | | |
| Minimum Viscosity, t5 (minutes) | 40.2 | 46.7 |
| Scorch, t5 (minutes) | 14.5 | 16.7 |
| Oscillating Disk Rheometer @ 171° C. | | |
| Minimum Torque (inch-pounds) | 0.7 | 0.9 |
| Maximum Torque (inch-pounds) | 15.4 | 14.6 |
| Scorch time (ts2) | 2.9 | 3.5 |
| Cure time (tc90) (minutes) | 22.9 | 28.3 |

Although the invention has been illustrated by reference to specific embodiments, it will be apparent to those skilled in the art that various changes and modifications may be made which clearly fall within the scope of the invention, and are intended to be claimed.

We claim:

1. An additive comprising a dithiocarbamyl-1,3,4,-thiadiazole derivative having formula (I), or an isomer thereof:

$$XS-\underset{S}{\overset{N-N}{\diagup}}-S-S-\underset{\overset{\parallel}{S}}{C}-N\underset{R_2}{\overset{R_1}{\diagdown}} \quad (I)$$

where $R_1$ and $R_2$ are independently a radical being either an alkyl, a cycloalkyl, an alkenyl, an aryl, an arylalkyl, or an alkylaryl, or $R_1$ and $R_2$ together form a 3- to 7-membered cyclic ring structure; and X is (i) hydrogen, (ii) a dithiocarbamyl radical having formula (II):

$$S-\underset{\overset{\parallel}{S}}{C}-N\underset{R_4}{\overset{R_3}{\diagdown}} \quad (II)$$

where $R_3$ and $R_4$ are independently a radical being either an alkyl, a cycloalkyl, an alkenyl, an aryl, an arylalkyl, or an alkylaryl, or $R_3$ and $R_4$ together form 3- to 7-membered cyclic ring structure, or (iii) a mixture thereof.

2. The additive of claim 1, wherein X is hydrogen, and $R_1$ and $R_2$ are each ethyl.

3. The additive of claim 1, wherein X is hydrogen, and $R_1$ and $R_2$ are each isopropyl.

4. The additive of claim 1, wherein X is hydrogen, and $R_1$ and $R_2$ are each selected from the group consisting of butyl, isobutyl and mixtures thereof.

5. The additive of claim 1, wherein X is hydrogen, and $R_1$ and $R_2$ together form a 6-membered cyclic ring structure.

6. The derivative of claim 5, wherein the 6-membered cyclic ring structure is a piperidyl radical.

7. The additive of claim 1, further comprising a diluent.

8. A curable polymer composition comprising a major amount of at least one halogenated polymer and at least one additive comprising a dithiocarbamyl-1,3,4,-thiadiazole derivative having formula (I), or an isomer thereof:

$$XS-\underset{S}{\overset{N-N}{\diagup}}-S-S-\underset{\overset{\parallel}{S}}{C}-N\underset{R_2}{\overset{R_1}{\diagdown}} \quad (I)$$

where $R_1$ and $R_2$ are independently a radical being either an alkyl, a cycloalkyl, an alkenyl, an aryl, an arylalkyl, or an alkylaryl, or $R_1$ and $R_2$ together form a 3- to 7-membered cyclic ring structure; and X is (i) hydrogen, (ii) a dithiocarbamyl radical having formula (II):

$$S-\underset{\overset{\parallel}{S}}{C}-N\underset{R_4}{\overset{R_3}{\diagdown}} \quad (II)$$

where $R_3$ and $R_4$ are independently a radical being either an alkyl, a cycloalkyl, an alkenyl, an aryl, an arylalkyl, or an alkylaryl, or $R_3$ and $R_4$ together form 3- to 7-membered cyclic ring structure, or (iii) a mixture thereof.

9. The curable polymer composition of claim 8, wherein X is hydrogen, and $R_1$ and $R_2$ are each ethyl.

10. The curable polymer composition of claim 8, wherein X is hydrogen, and $R_1$ and $R_2$ are each isopropyl.

11. The curable polymer composition of claim 8, wherein X is hydrogen, and $R_1$ and $R_2$ are each selected from the group consisting of butyl, isobutyl and mixtures thereof.

12. The curable polymer composition of claim 8, wherein X is hydrogen, and $R_1$ and $R_2$ together form a 6-membered cyclic ring structure.

13. The curable polymer composition of claim 8, wherein the halogenated polymer is a chlorinated polymer.

14. The curable polymer composition of claim 13, wherein the chlorinated polymer is selected from the group consisting of homopolymers of epichlorohydrin, copolymers of epichlorohydrin and ethylene oxide or propylene oxide, polychloroprene, chlorinated polyolefins, chlorosulfonated polyolefin, polychloroalkylacrylates, chlorobutyl rubber and mixtures thereof.

15. The curable polymer composition of claim 13, wherein the chlorinated polyolefins is chloropolyethylene.

16. An additive comprising a dithiocarbamyl-bis-1,3,4,-thiadiazole derivative having formula (III), or an isomer thereof:

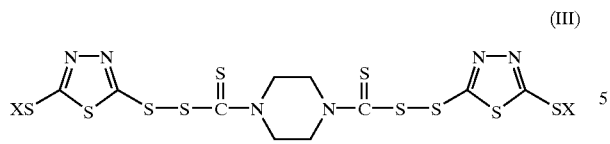

where X is (i) hydrogen, (ii) a dithiocarbamyl radical having formula (II):

where $R_3$ and $R_4$ are independently a radical being either an alkyl, a cycloalkyl, an alkenyl, an aryl, an arylalkyl, or an alkylaryl, or $R_3$ and $R_4$ together form 3- to 7-membered cyclic ring structure, or (iii) a mixture thereof.

17. The additive of claim 16, wherein X is hydrogen.

18. The additive of claim 16, further comprising a diluent.

19. A curable polymer composition comprising a major amount of at least one halogenated polymer and at least one additive comprising a dithiocarbamyl-bis-1,3,4,-thiadiazole derivative having formula (III), or an isomer thereof:

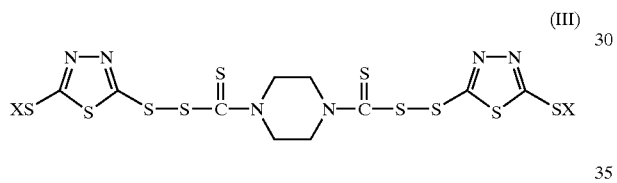

where X is (i) hydrogen, (ii) a dithiocarbamyl radical having formula (II):

where $R_3$ and $R_4$ are independently a radical being either an alkyl, a cycloalkyl, an alkenyl, an aryl, an arylalkyl, or an alkylaryl, or $R_3$ and $R_4$ together form 3- to 7-membered cyclic ring structure, or (iii) a mixture thereof.

20. The curable polymer composition of claim 19, wherein X is hydrogen.

21. The curable polymer composition of claim 19, wherein the halogenated polymer is a chlorinated polymer.

22. The curable polymer composition of claim 21, wherein the chlorinated polymer is selected from the group consisting of homopolymers of epichlorohydrin, copolymers of epichlorohydrin and ethylene oxide or propylene oxide, polychloroprene, chlorinated polyolefins, chlorosulfonated polyolefin, polychloroalkylacrylates, chlorobutyl rubber and mixtures thereof.

23. A method of preparing a cured polymer composition, which comprises:
 admixing at least one halogenated polymer with at least one additive including at least one thiadiazole derivative selected from the group consisting of:
 (a) a dithiocarbamyl-1,3,4,-thiadiazole derivative having formula (I), or an isomer thereof:

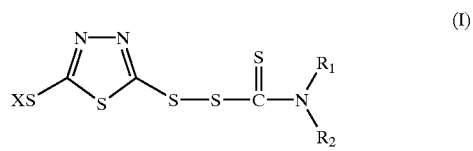

where $R_1$ and $R_2$ are independently a radical being either an alkyl, a cycloalkyl, an alkenyl, an aryl, an arylalkyl, or an alkylaryl, or $R_1$ and $R_2$ together form a 3- to 7-membered cyclic ring structure; and X is (i) hydrogen, (ii) a dithiocarbamyl radical having formula (II):

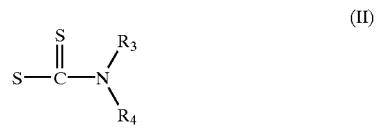

where $R_3$ and $R_4$ are independently a radical being either an alkyl, a cycloalkyl, an alkenyl, an aryl, an arylalkyl, or an alkylaryl, or $R_3$ and $R_4$ together form 3- to 7-membered cyclic ring structure, or (iii) a mixture thereof;

(b) a dithiocarbamyl-bis-1,3,4,-thiadiazole derivative having formula (III), or an isomer thereof:

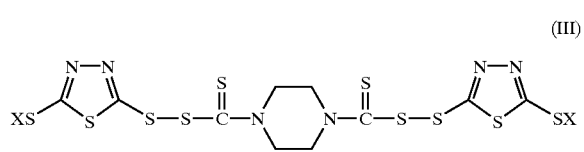

where X is (i) hydrogen, (ii) a dithiocarbamyl radical having formula (II):

where $R_3$ and $R_4$ are independently a radical being either an alkyl, a cycloalkyl, an alkenyl, an aryl, an arylalkyl, or an alkylaryl, or $R_3$ and $R_4$ together form 3- to 7-membered cyclic ring structure, or (iii) a mixture thereof; and curing the admixture to form the cured composition.

24. The method of claim 23, wherein at least one thiadiazole derivative is a derivative having formula (I), X is hydrogen, and $R_1$ and $R_2$ are each ethyl.

25. The method of claim 23, wherein at least one thiadiazole derivative is a derivative having formula (I), X is hydrogen, and $R_1$ and $R_2$ are each isopropyl.

26. The method of claim 23, wherein at least one thiadiazole derivative is the derivative having formula (I), X is hydrogen, and $R_1$ and $R_2$ are selected from the group consisting of butyl, isobutyl and mixtures thereof.

27. The method of claim 23, wherein at least one thiadiazole derivative is the derivative having formula (I), X is hydrogen, and $R_1$ and $R_2$ together form a 6-membered cyclic ring structure.

28. The method of claim 23, wherein at least one thiadiazole derivative is the derivative having formula (III) and X is hydrogen.

29. The method of claim 23, wherein the halogenated polymer is a chlorinated polymer.

30. The method of claim 29, wherein the chlorinated polymer is selected from the group consisting of homopolymers of epichlorohydrin, copolymers of epichlorohydrin and ethylene oxide or propylene oxide, polychloroprene, chlorinated polyolefins, chlorosulfonated polyolefin, polychloroalkylacrylates, chlorobutyl rubber and mixtures thereof.

31. The curable polymer composition of claim 29, wherein the chlorinated polyolefins is chloropolyethylene.

* * * * *